(12) United States Patent
Geiger et al.

(10) Patent No.: US 6,711,433 B1
(45) Date of Patent: Mar. 23, 2004

(54) METHOD FOR PROVIDING A VIRTUAL CONTRAST AGENT FOR AUGMENTED ANGIOSCOPY

(75) Inventors: Bernhard Geiger, Plainsboro, NJ (US); Nassir Navab, E. Windsor, NJ (US)

(73) Assignee: Siemens Corporate Research, Inc., Princeton, NJ (US)

(*) Notice: Subject to any disclaimer, the term of this patent is extended or adjusted under 35 U.S.C. 154(b) by 0 days.

(21) Appl. No.: 09/408,930

(22) Filed: Sep. 30, 1999

(51) Int. Cl.⁷ ................................................ A61B 6/00
(52) U.S. Cl. ................... 600/431; 600/420; 600/458; 378/98.11; 378/98.12; 378/42; 382/130
(58) Field of Search ................ 378/98.11, 98.12, 378/98.2, 41, 62, 42; 600/431, 420, 458, 425; 606/130; 382/130

(56) References Cited

U.S. PATENT DOCUMENTS

| | | | |
|---|---|---|---|
| 4,536,790 A | * 8/1985 | Kruger et al. | 358/111 |
| 4,888,794 A | 12/1989 | Haaker et al. | 378/41 |
| 5,315,630 A | 5/1994 | Sturm et al. | 378/65 |
| 5,369,678 A | * 11/1994 | Chiu et al. | 378/62 |
| 5,446,548 A | 8/1995 | Gerig et al. | 356/375 |
| 5,570,404 A | * 10/1996 | Liang et al. | 378/8 |
| 5,588,430 A | 12/1996 | Bova et al. | 128/653.1 |
| 5,644,613 A | * 7/1997 | Mick | 378/98.12 |
| 5,682,413 A | 10/1997 | Wong et al. | 378/98.11 |
| 5,690,106 A | * 11/1997 | Bani-Hashemi et al. | 128/653.1 |
| 5,772,594 A | 6/1998 | Barrick | 600/407 |
| 5,793,883 A | * 8/1998 | Kim et al. | 382/128 |
| 5,839,440 A | * 11/1998 | Liou et al. | 128/654 |
| 5,841,830 A | * 11/1998 | Barni et al. | 378/15 |

* cited by examiner

*Primary Examiner*—Dennis Ruhl
*Assistant Examiner*—Barry Pass

(57) ABSTRACT

A method for providing a virtual contrast agent for blood vessels in a body portion for angioscopy comprising deriving data from a 3D model using, for example, magnetic resonance imaging, computerized tomography (CT), and 3D angio. The data is segmented to provide a segmented 3D model of the blood vessels. A first procedure image is made with a contrast agent present. The 3D model is then registered with the first procedural image and "virtual camera parameters" are obtained. The 3D model is rendered and overlaid onto a second procedure image without contrast, whereby a virtual contrast is achieved.

15 Claims, 4 Drawing Sheets

METHOD FOR PROVIDING A VIRTUAL CONTRAST AGENT FOR AUGMENTED ANGIOSCOPY

BACKGROUND OF THE INVENTION

In many medical procedures, a catheter is inserted into the arterial system of a patient, and guided to a target location inside the body, this procedure being generally done under fluoroscopic guidance using a C-arm type of fluoroscopic apparatus. Periodically, the operating physician takes an X-ray snapshot to see where the tip of the catheter is located or, in the event of difficult manipulations, these are performed by the physician under constant fluoroscopic imaging.

Since blood vessels are essentially not visible on an X-ray image, contrast agent (CA) injected through the catheter whenever the operating physician needs to observe the position of the catheter with respect to the blood vessels. However, contrast agent is typically toxic, and the total amount of contrast agent that can be safely delivered to a patient is usually limited. It is herein recognized that a procedure that can reduce the amount of contrast agent is generally beneficial for the patient, because less contrast agent means less stress and fewer possible side effects on the patient and it decreases the risk of having to abort an intervention unsuccessfully because a limit of CA uptake has been reached.

SUMMARY OF THE INVENTION

In accordance with an aspect of the invention, a method for providing a virtual contrast agent for blood vessels in a body portion, comprising the steps of: acquiring data for a 3D model from an imaging process; segmenting the data to provide a segmented 3D model of the blood vessels; obtaining a first procedure image of the body portion utilizing a radiation source and an image detector, the procedure image including the blood vessels with contrast agent injection; registering the segmented 3D model with the procedure image, and deriving therefrom parameters relating the positions of the body portion, the radiation source, the image detector, and the 3D model; obtaining a second procedure image of the body portion utilizing the radiation source and the image detector, the second procedure image being obtained without contrast agent injection; and rendering the 3D model and overlaying the 3D model onto the second procedure image. The procedure image is the image used during the intervention procedure.

In accordance with another aspect of the invention, a method for providing a virtual contrast agent includes the step of acquiring data for a 3D model from an imaging process, wherein the imaging process comprises one of magnetic resonance imaging, computerized tomography (CT), and 3D angio, and the procedure images comprises one of magnetic resonance imaging, computerized tomography (CT), 3D angio, fluoroscopy, and ultrasound imaging.

In accordance with still another aspect of the invention, a method for providing a virtual contrast agent for blood vessels in a body portion, comprising the steps of: acquiring data for a 3D model from an imaging process; segmenting the data to provide a segmented 3D model of the blood vessels; obtaining a first procedure image of the body portion utilizing a radiation source and an image detector, the first procedure image including the blood vessels with contrast agent injection; registering the segmented 3D model with the procedure image, and deriving therefrom parameters relating the positions of the body portion, the radiation source, the image detector, and the 3D model by comparing the first procedure image with a number of precalculated projections of the 3D model; obtaining a second procedure image of the body portion utilizing the radiation source and the image detector, the second procedure image being obtained without contrast agent injection; and rendering the 3D model by finding a catheter tip in the second procedure image by rendering a subset of the segmented 3D model including the catheter tip and downstream blood vessel portions; and overlaying the 3D model onto the second procedure image utilizing virtual contrast.

In accordance with still another aspect of the invention, a method for providing a virtual contrast agent for blood vessels in a body portion for angioscopy comprises deriving data from a 3D model using, any of magnetic resonance imaging, computerized tomography (CT), and 3D angio; segmenting the data to provide a segmented 3D model of the blood vessels; generating a first procedure image with a contrast agent present; registering the 3D model with the first procedural image and thereby obtaining "virtual camera parameters"; rendering the 3D model; and overlaying the rendered 3D model onto a second procedure image without contrast, whereby a virtual contrast is achieved.

An object of the present invention is to reduce the amount of contrast agent during an intervention using a catheter inside the arterial tree.

BRIEF DESCRIPTION OF THE DRAWINGS

The invention will be more fully understood from the detailed description of preferred embodiments which follows, in conjunction with the Drawing, in which.

DETAILED DESCRIPTION OF THE PREFERRED EMBODIMENT

In accordance with an aspect of the invention, a 3D reconstruction of the arterial tree is calculated prior to the intervention. This can be made from a computerized tomography (CT) acquisition, or from magnetic resonance imaging (MRI), or from 3D angio, as known other contexts. See, for example, N. Navab et al., "3D reconstruction from projection matrices in a C-arm based 3d-angiography system.", in First International Conference on Medical Image Computing and Computer-Assisted Intervention (MICCAI), pp. 1305–1306, Cambridge, Mass.; 1998.

An on-line registration of the 3D reconstruction with a fluoroscopic image or images and the catheter is carried out during the intervention. A 2D virtual contrast injection image is calculated from the 3D reconstruction and is then added to the fluoroscopic image in a way as to imitate the effect of a contrast injection. The physician sees the fluoroscopic image showing the catheter, and the blood vessels are blended in from the 3D model, thereby resulting in a virtual contrast injection. In practice, in accordance with an aspect of the invention, the physician can decide whether to activate the real contrast injection or the virtual contrast injection. Occasionally it is necessary to use the real contrast injection to update registration. For example, one out of two, or two out of three injections could be replaced by a virtual injection which is not associated with the potential harm to the patient of a contrast injection.

There are several advantages to such a procedure in accordance with the invention. Among these is the fact that the amount of contrast agent required to be administered is reduced. The physician uses the procedure in an accustomed and familiar way so that in watching the fluoroscopic display, the physician sees the images in the customary manner. The system in accordance with the invention is seamlessly integrated into the clinical routine and the physician can switch between virtual and real contrast. Virtual contrast can be used on passages that are less critical while real contrast can be selected for use in parts where the physician does not want to rely on the registration. Furthermore, in accordance with an aspect of the invention, the physician can have a full 3-dimensional rendering on an additional screen in addition to the augmented fluoroscopic image.

Figure 1:
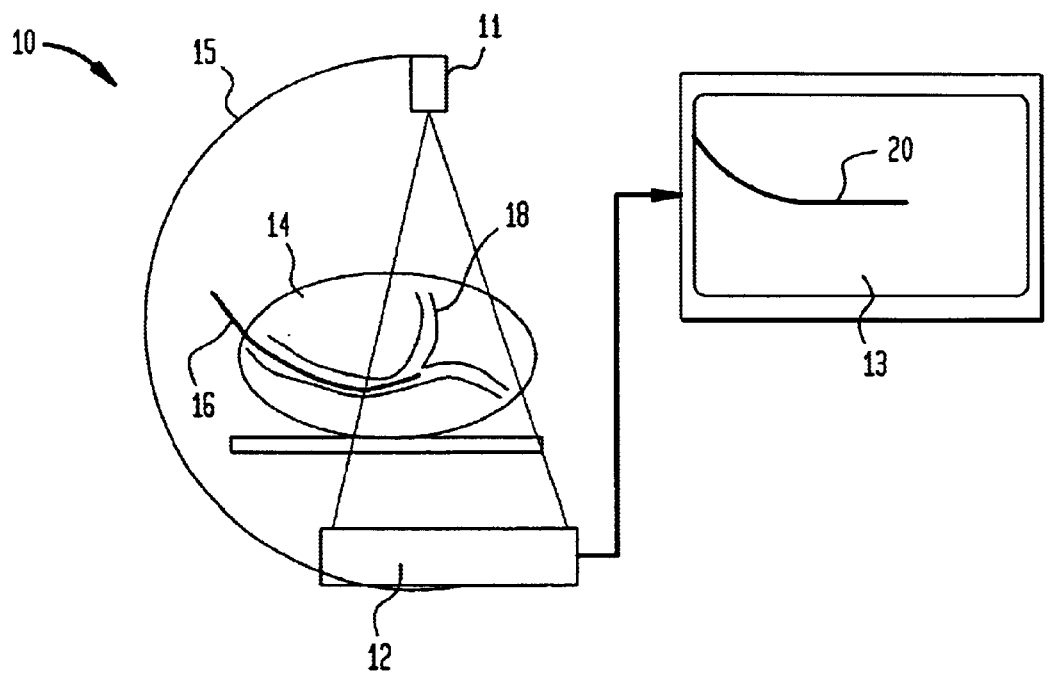
FIG. 1 shows in diagrammatic form a set-up in accordance with an aspect of the invention.

FIG. 1 shows in diagrammatic form an x-ray apparatus or fluoroscope 10, including a radiation source 11, a detector 12 and a screen 13 for examining a person's body 14. Source 11 and detector 12 are mounted in a known manner to a C-arm 15. A catheter 16 is inserted into a blood vessel 18 of body 14. As is known, catheter 16 will be visible on screen 13, herein indicated as image portion 20 on screen 13, but blood vessel 18 will not be visible.

Figure 2:
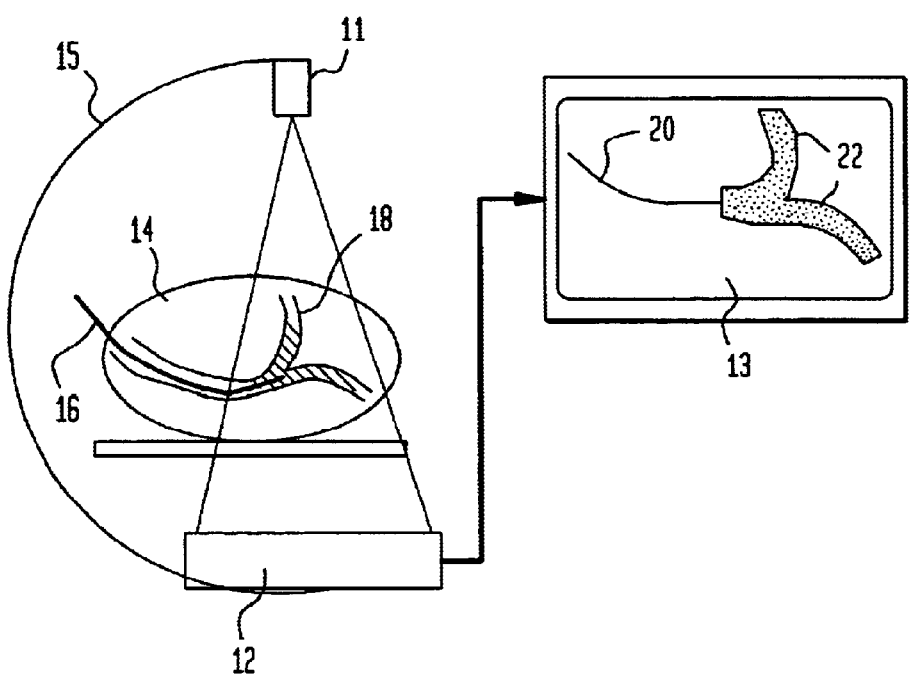
FIG. 2 shows in diagrammatic form the use of a contrast agent.

FIG. 2 shows the effect of injecting a contrast agent into body 14 so that blood vessels around the tip of catheter 16 show up on the fluoroscopic image on screen 13 as image portions 22.

Figure 3:
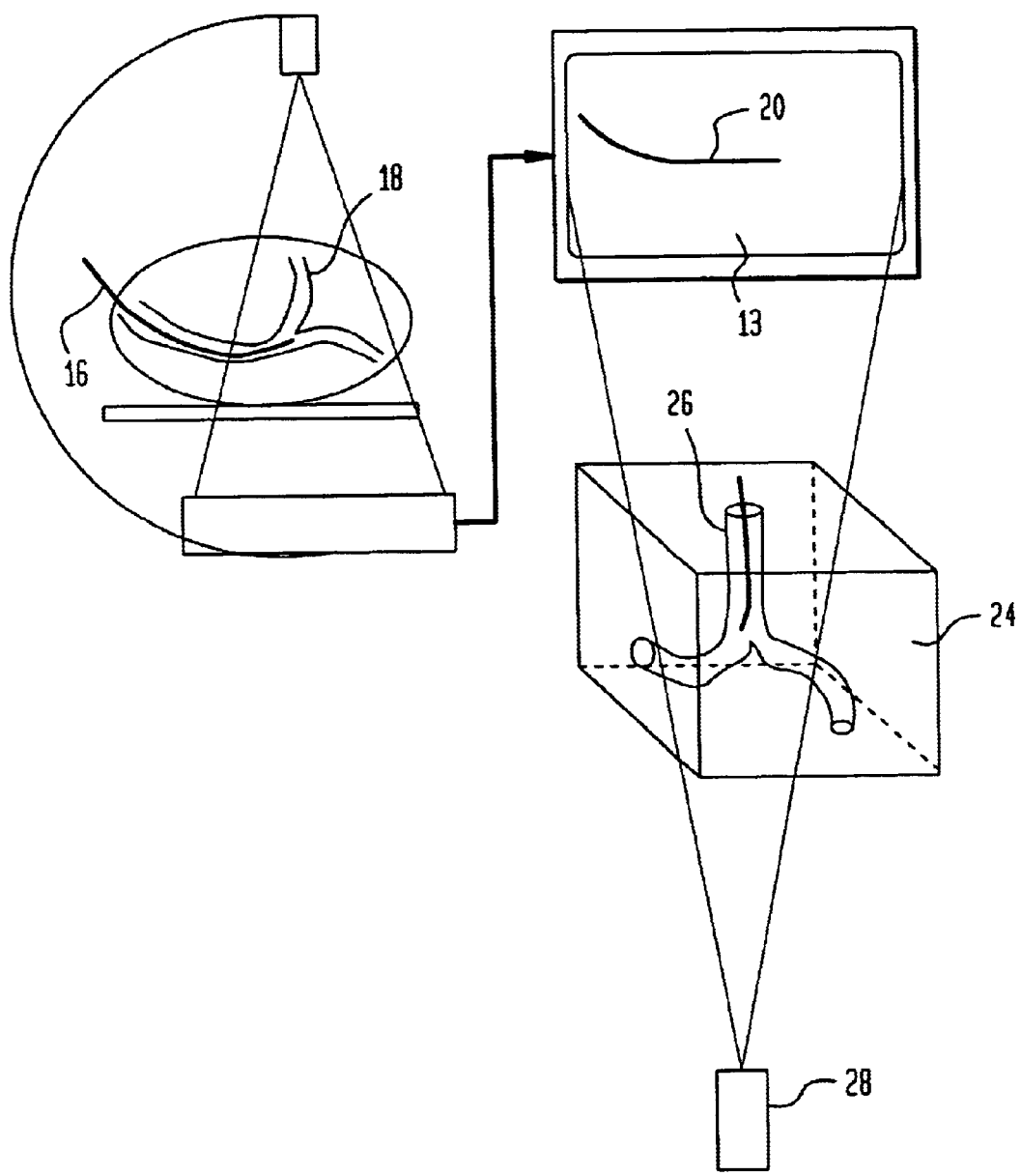
FIG. 3 shows the use of a 3D model in accordance with an aspect of the invention and without the use of real contrast agent.

FIG. 3 shows a configuration in accordance with an embodiment of the present invention with a computerized 3D model 24 of an arterial tree 26 which is generated using a computer (not shown).

Information for producing 3D model 24 of an arterial tree is derived from magnetic resonance angiograpy (MRA), computerized tomography angiography (CTA), or three-dimensional (3D) angiographic examination (angio exam). Furthermore, 28 is the position of a "virtual camera", representative of a view-point which, when used to render the 3D model 24, produces an image similar to the fluoroscopic image on 13. Camera parameters, such as projection angles, relating to fluoroscope 10 and information on the registration procedure are required.

At any given moment, the computerized 3D model is in registration with the fluoroscope and the patient. This means that the projection parameters of the x-ray configuration are known to the computer (not shown) which produces the computerized 3D model. The computer (not shown) is used to produce a "virtual" x-ray image from the 3D model, using the geometry information for the actual C-arm. The position of the catheter tip inside the 3D model is also known from a registration process.

Figure 4:
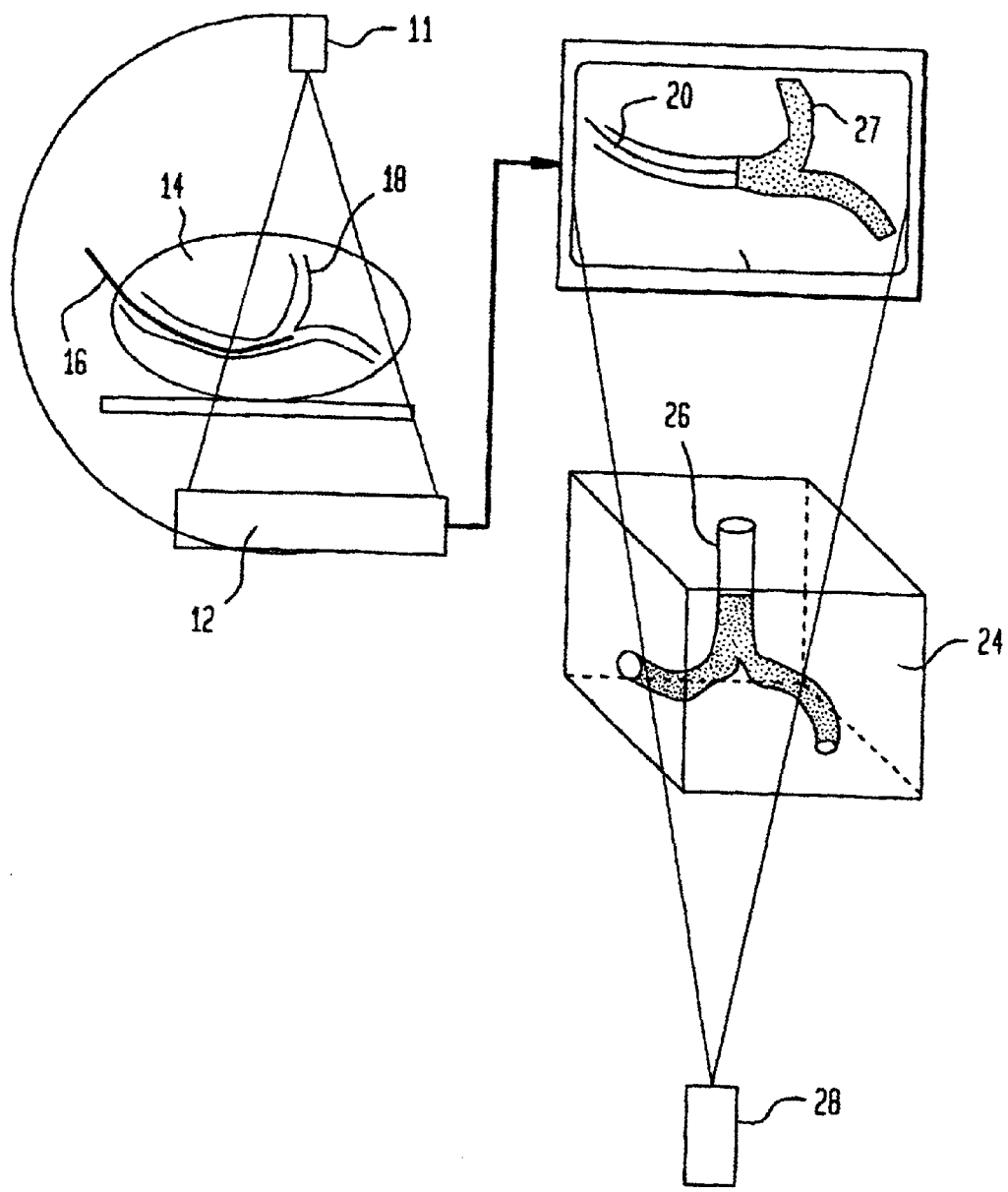
FIG. 4 shows the use of virtual contrast in accordance with an aspect of the invention.

As shown in FIG. 4, the "virtual contrast" has been calculated in accordance with an embodiment of the present invention by rendering the blood vessels of the 3D model around the tip of the catheter, using the same geometry as pertains to the C-arm. Briefly, this means that the 3D information on the blood vessels is used to provide a 2D image of the blood vessels, corresponding to the position of the C-arm so as to simulate what would be seen from that position with the use of a contrast agent.

In accordance with an embodiment of the present invention, the images 27 thus created of the blood vessels are overlayed over the fluoroscopic image. The virtual contrast can be rendered in a predetermined, or artificial color so as to make it plainly evident to the physician that real contrast is not being used. Alternatively, the contrast can be rendered by another image characterstic such as "flashing" the image or causing it to blink. Since a 3D rendering of the catheter location is produced and overlayed at the same time, and the real catheter is always visible on the fluoroscopic image without contrast injection, the physician has a visual control of the accuracy of the registration: if there is a discrepancy in the registration, the physician should then use a real contrast image in order to re-register the data.

Figure 5:
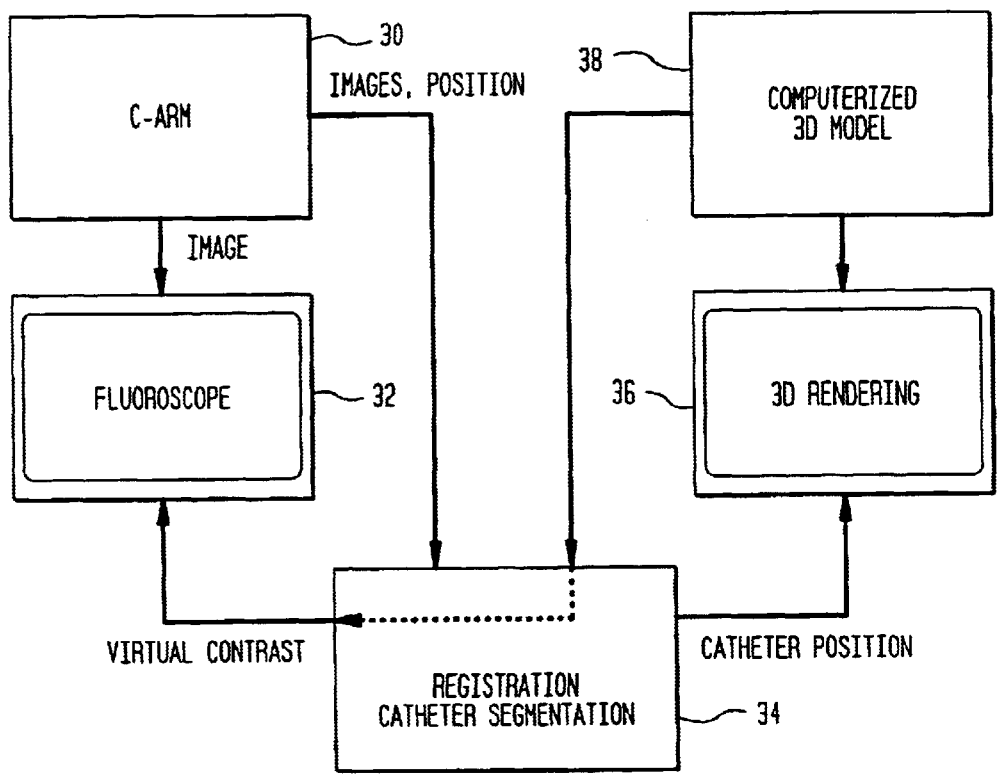
FIG. 5 shows in block diagram form components in accordance with the principles of the invention.

FIG. 5 shows the components of the system in accordance with an embodiment of the present invention and their interaction. On the left side, the C-arm 30 and fluoroscope 32 send images and information about the projection (position and orientation) of the C-arm to the registration system 34. The registration system computes the transformation between 3D model 38 and the C-arm system. From this transformation, the position of the tip of the catheter in the 3D model 38 is calculated.

The rendering system 36 can then produce a 2D projection of the 3D model 38 that shows the 3D model in a "virtual " fluoroscopic view. The 3D model 38 can optionally be shown completely, or as selected parts only. For example, it may be desirable to show only the part of the 3D model from the tip of the catheter in direction of the blood flow. This would show the surgeon a view similar to the view obtained when the contrast agent is flowing into the blood vessel through the catheter. However, in accordance with the present invention, no contrast agent is needed.

On the computer screen shown on the right in FIG. 5, the surgeon can see a rendering of the 3D model, and an indicator that shows the tip of the catheter or, as the case may be, the endoscope.

The surgeon can decide whether a real injection of contrast agent or a "virtual" contrast injection is needed. If a real injection is selected, the image from fluoroscope 32 in FIG. 5, is sent to the registration unit, and the 3D model gets re-registered with the image.

Figure 6:
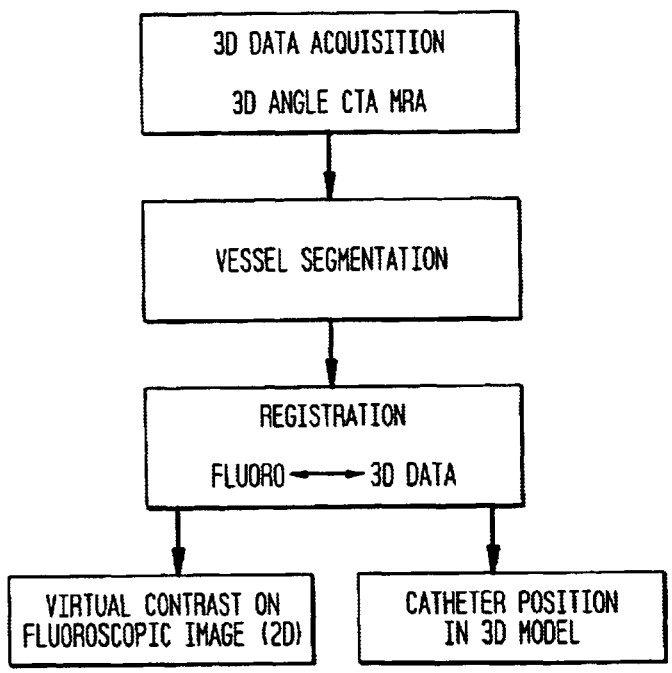
FIG. 6 shows a flow chart helpful to an understanding of the invention.

FIG. 6 shows steps to be performed in accordance with an embodiment of the present invention.

A 3D model of the vessel tree is constructed utilizing segmentation. From 3D angio data, CTA or MRA data, the vessel tree can be segmented using commercially available proprietary systems such as "3D virtuoso". The techniques used are thresholding and/or region growing. Segmentation is a standard procedure that can be done with commerially available products. It is a procedure to identify the voxels in a volumetric dataset, (such as obtained form MRI, CT, or 3D angio) that belong to a specific organ (such as the arteries). The result of a segmentation is a binary classification where each voxel is classified into "is part of object" or "is not part of object".

Before segmentation, each voxel has a value that is determined by a physical property of the tissue (density, x-ray absorption, etc, dependent on the imaging modality). After the segmentation, each voxel has either the value 1 (part of object) or 0 (not part of object). The most commonly used segmentation methods are thresholding and region growing. In thresholding, the user specifies an upper and a lower threshold. The voxels with a value in between these thresholds are selected as being part of the object, all others are classified as not being path of the object.

In region growing, there is one more input necessary: in addition to the lower and upper threshold, a geometric location has to be selected which is known to be part of the object (seed). Then, in accordance with a known technique, only voxels with values in between the threshold and having a link with that seed are taken as being part of the object.

A segmentation can be used in a commercially available rendering system (such as 3D Virtuoso, or Magicview) to produce an image of the segmented object.

In the present application, a segmentation of arteries is necessary, herein referred to as a segmentation vessel tree, since the arteries have generally the shape of a tree, wherein an artery splits into smaller branches. The blood flow is directed from the larger vessel towards the smaller vessels. The largest vessel, or the vessel from which the blood flow originates is referred to as the start of the vessel tree, or the root.

The process in accordance with the invention for providing a virtual contrast agent further requires additional information representing the position of the tip of the catheter and the blood flow direction. This is needed to decide which part of the vessel tree has to be rendered if a virtual contrast injection is considered to take place at a particular location.

The position of the tip of the catheter (toc) can be found by doing a binary segmentation of either a fluoroscopic image without contrast, or of a subtracted image. Image subtraction is a frequently used technique for fluoroscopy where an image without contrast is stored and later subtracted from an image made with injected contrast material, thereby providing a subtracted image with, for example, bone images removed thereby leaving blood vessels more clearly visible.

In most cases, the catheter is well defined in the fluoroscopic image, so that a simple thresholding would be sufficient to identified the pixels that represent the catheter.

In other cases, where the contrast attained by thresholding is sufficient, a previously stored image without the catheter can be subtracted from the image with catheter.

The segmented image of the catheter shows a line image of the catheter that crosses the image border and has one free end. See, for example 20 in FIG. 3. The toc can be identified in the image as the end of the line that does not cross the image border and that is therefore present in the body of the image.

The point representing the image of the tip of the catheter, together with the information found from the registration process, including the "view-point" and the projection angles, defines a straight line in 3D space. The toc in 3D is at the intersection point of this line with the 3D model.

In accordance with an aspect of the invention the flow direction information can be obtained by using a region growing in the binary segmented vessel tree that starts at the base of the vessel tree.

In accordance with an aspect of the invention, a user can interactively select a voxel at the base of the vessel tree. This voxel gets a label 0. All voxels in the vessel that are adjacent to that voxel get the label 1. All voxels adjacent to voxels with label n get the label (n+1). For virtual contrast, if the tip of the catheter is found to be in voxel m, the rendering system would only render voxels with a label $\geq$ m and linked to the same voxel.

In the registration procedure in accordance with the principles of the invention, the fluoroscopic image during a real contrast injection is registered with the 3D model. Since the contrast agent will fill a larger part of the vessel tree than the catheter, accuracy of registration will be higher.

The viewing angle of the fluoroscopic projection is known from physical data for the installation as is the positioning of the patient in the C-arm system, that is, supine or other. Typically, the surgical operator will have selected a viewpoint for the c-arm that provides an optimal view of a particular vessel, preferably so that there are no other vessels covered by other vessels, or other such ambiguities.

The registration of the 3 dimensional model with the fluoroscopic images can be done in several alternative ways in accordance with the principles of the invention One technique uses a number of precalculated projections of the 3D model that are compared to the so actual fluoroscopic images. The closest match is then considered to give the best registration. This technique, in itself is known from A. Schweikard et al., "Treatment planning for a radiosurgical system with general kinematics," IEEE International Conference on Robotics and Automation, pp. 1720–1727, San Diego; May 1994, IEEE Computer Society Press.

Another technique utilizes fiducial markers on the patient that are visible in the 3D model as well as from an optical tracker in the radiology suite, thereby making possible a correlation for providing registration.

Yet another technique applicable to the present invention is to utilize an off-line calibration of the C-arm, as disclosed by Navab. As long as the patient position does not change, this results in a calibrated system where the projection matrices of the C-arm are known. However, while this is possibly the easiest technique to implement, it is only possible if the model is obtained from 3D angio using the same C-arm and the same calibration. In contrast, the other techniques described will work with general models, including MRA and CTA.

While the present invention has been described by way of exemplary embodiments, it will be understood by those of skill in the art to which it pertains that various modifications and changes may be made without departing from the spirit of the invention which is defined by the claims following.

What is claimed is:

1. A method for providing a virtual contrast agent for blood vessels in a body portion, comprising the steps of:

acquiring data for a 3D model from an imaging process;

segmenting said data to provide a segmented 3D model of said blood vessels;

obtaining a first procedure image of said body portion utilizing a radiation source and an image detector, said first procedure image including said blood vessels with contrast agent injection;

registering said segmented 3D model with said first procedure image, and deriving therefrom parameters relating positions of said body portion, said radiation source, said image detector, and said 3D model;

obtaining a second procedure image of said body portion utilizing said radiation source and said image detector, said second procedure image being obtained without contrast agent injection;

rendering said 3D model and overlaying a 2D projection of said 3D model onto said second procedure image; and simulating a contrast agent injection on said second procedure image, said simulated injection being calculated by said 3D model.

2. A method for providing a virtual contrast agent as recited in claim 1 wherein said imaging process comprises one of magnetic resonance imaging, computerized tomography (CT), and 3D angio, and said first and second procedure images comprise one of magnetic resonance imaging, computerized tomography (CT), 3D angio, fluoroscopy, and ultrasound imaging.

3. A method for providing a virtual contrast agent as recited in claim 1 wherein said step of segmenting comprises labeling blood flow direction in said blood vessels.

4. A method for providing a virtual contrast agent as recited in claim 1, wherein said step of rendering comprises a step of finding a catheter tip in said second procedure image and rendering a subset of said segmented 3D model including said catheter tip and downstream blood vessel portions.

5. A method for providing a virtual contrast agent as recited in claim 4, wherein said step of finding a catheter tip comprises thresholding of said second procedure image to produce a thresholded image.

6. A method for providing a virtual contrast agent as recited in claim 5, comprising the step of identifying as the tip of said catheter as the end of a line that does not cross the image border and that is therefore located within the border of said thresholded second procedure image.

7. A method for providing a virtual contrast agent as recited in claim 6, wherein said step of finding a catheter tip comprises the steps of finding said catheter tip in said 3D model by:
deriving a straight line in 3D space from said parameters relating positions of said body portion, said radiation source, said image detector, and said 3D model and said tip of said catheter in said second procedure image; and
determining the intersection point of said straight line with said 3D model.

8. A method for providing a virtual contrast agent as recited in claim 4, wherein said step of finding a catheter tip comprises the steps of:
deriving a subtracted image by subtracting a previously stored image without contrast and without a catheter from said second procedure image with catheter;
thresholding said subtracted image; and
identifying as the tip of said catheter in said subtracted image as the end of a line that does not cross the image border and that is therefore located within the border of said subtracted image.

9. A method for providing a virtual contrast agent as recited in claim 8, wherein said step of finding a catheter tip comprises the steps of finding said catheter tip in said 3D model by:
deriving a straight line in 3D space from said parameters relating the positions of said body portion, said radiation source, said image detector, and said 3D model and said tip of said catheter In said subtracted image; and
determining an intersection point of said straight line with said 3D model.

10. A method for providing a virtual contrast agent as recited in claim 1, wherein said rendering and overlaying is selectively performed using virtual contrast.

11. A method for providing a virtual contrast agent as recited in claim 10, wherein said virtual contrast is performed utilizing a contrasting color.

12. A method for providing a virtual contrast agent as recited in claim 10, wherein said virtual contrast is performed utilizing intensity modulation.

13. A method for providing a virtual contrast agent for blood vessels in a body portion, comprising the steps of:
acquiring data for a 3D model from an imaging process;
segmenting said data to provide a segmented 3D model of said blood vessels;
obtaining a first procedure image of said body portion utilizing a radiation source and an image detector, said first procedure image including said blood vessels with contrast agent injection;
registering said segmented 3D model with said first procedure image, and deriving therefrom parameters relating the positions of said body portion, said radiation source, said image detector, and said 3D model by comparing said first procedure image with a number of precalculated projections of said 3D model;
obtaining a second procedure image of said body portion utilizing said radiation source and said image detector, said second procedure image being obtained without contrast agent injection;
rendering said 3D model by finding a catheter tip in said second procedure image by rendering a subset of said segmented 3D model including said catheter tip and downstream blood vessel portions; and
overlaying a 2D projection of said 3D model onto said second procedure image utilizing virtual contrast.

14. A method for providing a virtual contrast agent for blood vessels in a body portion, comprising the steps of:
deriving data for a 3D model;
segmenting said data to provide a segmented 3D model of said blood vessels;
generating a first procedure image with a contrast agent present;
registering said segmented 3D model with said first procedure image and thereby obtaining virtual camera parameters;
rendering said 3D model; and
overlaying a 2D projection of said 3D model onto a second procedure image without contrast, whereby a virtual contrast is achieved by simulating a contrast agent injection in said rendered 3D model.

15. A method for providing a virtual contrast agent for blood vessels in a body portion, comprising the steps of;
acquiring data for a 3D model from an imaging process;
segmenting said data to provide a segmented 3D model of said blood vessels;
obtaining a first procedure image of said body portion utilizing a radiation source and an image detector, said first procedure image including said blood vessels with contrast agent injection;
registering said segmented 3D model with said first procedure image, and deriving therefrom parameters relating positions of said body portion, said radiation source, said image detector, and said 3D model;
obtaining a second procedure image of said body portion utilizing said radiation source and said image detector, said second procedure image being obtained without contrast agent injection; and
rendering said 3D model and overlaying a 2D projection of said 3D model onto said second procedure image, wherein said step of rendering further comprises the step of finding a catheter Up in said second procedure image by deriving a subtracted image by subtracting a previously stored image without contrast and without a catheter from said second procedure image with said catheter, thresholding said subtracted image, and identifying as the tip of said catheter in said subtracted image as the end of a line that does not cross the subtracted image border and that is therefore located within the border of said subtracted image; and rendering a subset of said segmented 3D model including said catheter tip and downstream blood vessel portions by deriving a straight line in 3D space from said parameters relating the positions of said body portion, said radiation source, said image detector, and said 3D model and said tip of said catheter in said subtracted image, and determining the intersection point of said straight line with said 3D model.

* * * * *